(12) United States Patent
House

(10) Patent No.: US 8,317,775 B2
(45) Date of Patent: Nov. 27, 2012

(54) URINARY CATHETERIZATION ASSEMBLY WITH VENTED SHEATH

(75) Inventor: Jamie Glen House, Colorado Springs, CO (US)

(73) Assignee: Adapta Medical, Inc., Colorado Springs, CO (US)

( * ) Notice: Subject to any disclaimer, the term of this patent is extended or adjusted under 35 U.S.C. 154(b) by 1217 days.

(21) Appl. No.: 11/652,527

(22) Filed: Jan. 12, 2007

(65) Prior Publication Data

US 2007/0225649 A1 Sep. 27, 2007

Related U.S. Application Data

(60) Provisional application No. 60/781,225, filed on Mar. 10, 2006.

(51) Int. Cl.
*A61M 27/00* (2006.01)

(52) U.S. Cl. .................................................. 604/544

(58) Field of Classification Search .............. 604/544, 604/445

See application file for complete search history.

(56) References Cited

U.S. PATENT DOCUMENTS

| | | | | |
|---|---|---|---|---|
| 3,672,372 | A * | 6/1972 | Heimlich | 604/544 |
| 4,622,033 | A | 11/1986 | Taniguchi | |
| 4,772,275 | A | 9/1988 | Erlich | |
| 4,834,710 | A | 5/1989 | Fleck | |
| 4,867,747 | A * | 9/1989 | Yarger | 604/263 |
| 5,149,326 | A | 9/1992 | Woodgrift et al. | |
| 5,181,913 | A | 1/1993 | Erlich | |
| 5,779,670 | A | 7/1998 | Bidwell et al. | |
| 5,792,114 | A | 8/1998 | Fiore | |
| 5,895,374 | A | 4/1999 | Rodsten | |
| 6,053,905 | A | 4/2000 | Daignault et al. | |
| 6,059,107 | A | 5/2000 | Nosted et al. | |
| 6,090,075 | A | 7/2000 | House | |
| 6,132,405 | A * | 10/2000 | Nilsson et al. | 604/264 |
| 6,176,849 | B1 | 1/2001 | Yang et al. | |
| 6,217,569 | B1 | 4/2001 | Fiore | |
| 6,409,717 | B1 | 6/2002 | Israelsson et al. | |
| 6,471,684 | B2 | 10/2002 | Dulak et al. | |
| 6,578,709 | B1 | 6/2003 | Kavanagh et al. | |
| 6,602,244 | B2 | 8/2003 | Kavanagh et al. | |
| 6,634,498 | B2 | 10/2003 | Kayerod et al. | |
| 6,673,053 | B2 | 1/2004 | Wang et al. | |
| 6,736,805 | B2 | 5/2004 | Israelsson et al. | |
| 6,848,574 | B1 | 2/2005 | Israelsson et al. | |
| 2001/0001443 | A1 | 5/2001 | Kayerod et al. | |
| 2001/0007060 | A1 | 7/2001 | Fiore | |
| 2001/0027295 | A1 | 10/2001 | Dulak et al. | |
| 2001/0027299 | A1 | 10/2001 | Yang et al. | |
| 2003/0018302 | A1 | 1/2003 | Kavanagh et al. | |
| 2004/0074794 | A1 | 4/2004 | Conway et al. | |
| 2004/0153051 | A1 | 8/2004 | Israelsson et al. | |
| 2004/0256264 | A1 | 12/2004 | Israelsson et al. | |
| 2005/0015076 | A1 | 1/2005 | Giebmeyer et al. | |
| 2005/0085841 | A1 | 4/2005 | Eversull et al. | |
| 2005/0109648 | A1 | 5/2005 | Kerzman et al. | |
| 2005/0137582 | A1 | 6/2005 | Kull-Osterlin et al. | |
| 2006/0025753 | A1 | 2/2006 | Kubalak et al. | |
| 2008/0091136 | A1* | 4/2008 | House | 604/23 |

* cited by examiner

*Primary Examiner* — Kevin C Sirmons
*Assistant Examiner* — Ginger T Chapman
(74) *Attorney, Agent, or Firm* — Moazzam & Associates, LLC

(57) ABSTRACT

A urinary catheter assembly is disclosed having a catheter, a sheath enclosing an insertable portion of the catheter, and one or more vents in fluid communication with the lumen of the sheath and an environment outside the sheath.

15 Claims, 6 Drawing Sheets

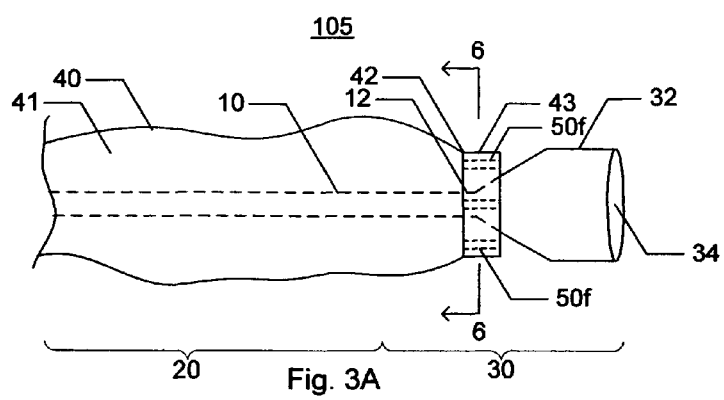
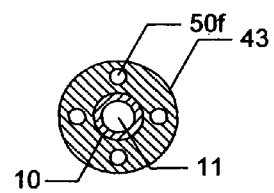
Fig. 3A　　　　　　　　　　Fig. 3B
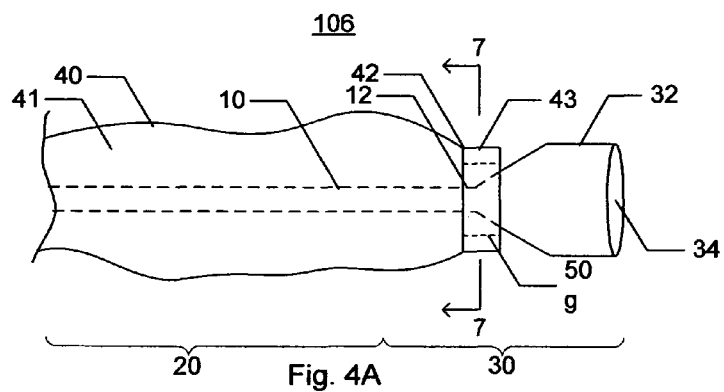
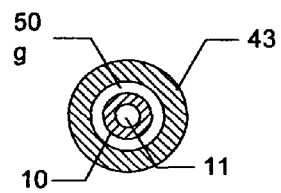
Fig. 4A　　　　　　　　　　Fig. 4B

URINARY CATHETERIZATION ASSEMBLY WITH VENTED SHEATH

This application claims priority to U.S. Provisional Patent Application Ser. No. 60/781,225, filed Mar. 10, 2006, the content of which is hereby incorporated by reference in its entirety into this disclosure.

BACKGROUND OF THE INVENTION

1. Field of the Invention

The present disclosure is directed to devices and methods for catheterization of the urinary bladder. More particularly, the present invention relates to such devices and methods employing a sheathed catheter.

2. Background of the Invention

The occasional or periodic catheterization of an individual's urinary bladder is a common practice today for many persons who are in a hospital setting, a nursing home, doctor's office, rehabilitation facility or at home. For instance, a patient may be catheterized to treat such conditions as urinary retention, the inability to evacuate urine, or for the purpose of obtaining a sterile urine specimen from a patient in a doctor's office.

Generally, catheterizations may be assisted (non self-catheterizations) or unassisted (self-catheterizations). In assisted catheterizations, a nurse may perform the catheterization by employing a catheterization tray ("cath tray"), which typically includes a sterile drape, gloves, a conventional catheter, antiseptic solution, cotton balls, lubricant, forceps, underpad and a urine collection container. All of these items are typically packaged together and sterilized. However, to perform the catheterization, the nurse must open the tray and handle the various items in the tray. Although special precautions may be taken, maintaining a sterile environment during the procedure may present challenges. Further, because multiple steps are involved in the procedure, a nurse may spend a significant amount of time (e.g., 10-15 minutes) carrying out each catheterization. In addition, conventional "cath tray" procedures may be expensive or otherwise impractical for use with some individuals and situations today.

For some of the above-stated reasons, many individuals, if capable, would prefer to perform self-catheterization. For many, the level of risk and discomfort of repeated catheterizations carried out over the course of a day (e.g., at 3-6 hour intervals) are offset by the accompanying convenience, privacy or self-reliance that is achieved. Some of the major difficulties that arise in self-catheterization are problems relating to maintaining the required level of sanitation during the procedure, and the difficulty of sometimes performing the procedure under conditions of restricted space and privacy.

A variety of catheterization kits and products are currently available. For instance, U.S. Pat. No. 6,090,075 (House I) discloses a catheter assembly with a catheter introducer member for positioning catheter assembly against the urethral opening, a flexible catheter, and a flexible thin-walled sheath surrounding the catheter and partially covering the catheter introducer.

Some catheterization assemblies and kits employ hydrophilic catheters that are self-lubricating when wetted with a fluid (e.g., water) prior to use. U.S. Pat. No. 6,409,717 (Astra Aktiebolag) and U.S. Pat. No. 6,736,805 (AstraZeneca AB) describe apparatus for wetting a hydrophilic urinary catheter, having a wetting receptacle which defines a wetting fluid receiving area for receiving the catheter and a wetting fluid container having a discharge outlet movable from a closed position to an open position on application of a predetermined condition thereto to enable the wetting fluid to be discharged from the container. U.S. Pat. No. 6,634,498 (Coloplast A/S) describes certain urinary catheter assemblies including a urinary catheter having at least a part of its surface a hydrophilic surface layer intended to produce a low-friction surface character of the catheter by treatment with a liquid swelling medium during manufacture of the catheter assembly, and a catheter package having a cavity for accommodation of the catheter. The package includes a compartment having walls of a gas impermeable material that accommodates the liquid swelling medium and a pre-treated catheter for long term preservation of the low-friction surface character and provision of a ready-to-use catheter assembly.

Some catheter assemblies include a protective sheath that surrounds the catheter or a portion thereof. The sheath may serve multiple purposes. For instance, the sheath may prevent contamination of the catheter as the catheter is handled prior to and/or during use. In addition, in some hydrophilic catheters, the sheath may contain a wetting agent used to lubricate the catheter during use. Failure of the sheath may lead to various problems, such as urinary tract infections, pain, and/or difficult catheterizations.

In some instances, a flexible catheter sheath is gathered near the distal end of the catheter (e.g., end relatively away from the patient) during use to allow the catheter to advance beyond the sheath and into the patient's urethra. As the sheath is gathered, the volume within the sheath may decrease. In assemblies in which the sheath lumen is not in fluid communication with a collection receptacle or the environment outside the sheath, some fluid contained within the sheath (e.g., air, wetting agent, etc.) may become trapped and compressed, resulting in a pressure buildup within the sheath (e.g., the sheath may "balloon-up"). A slight to moderate pressure build-up within the sheath may not result in any problems; however, excessive pressure build-up within the sheath may lead to noticeable problems. For example, excessive pressure buildup within the sheath may result in forces opposing further gathering of the sheath, thereby limiting the degree to which the catheter may be advanced into the urethra. In addition, as a consequence of an excessive pressure build-up, the sheath may "balloon-up," potentially limiting the ability of the user to adequately grasp the catheter through the sheath. This consequence may detrimentally affect the ability of the user to control and manipulate the catheter during insertion. Further, an extreme pressure build-up may cause the sheath to rupture, potentially compromising the ability of the sheath to prevent contamination of the catheter contained within. In addition, a tear or rupture in the sheath may detrimentally impact the ability of the sheath to contain a wetting agent (e.g., hydrophilic catheters), create a clean-up nuisance, and possibly result in an unexpected, abrupt movement of the catheter. In instances in which excessive pressure-build-up within the sheath could arise, it would be advantageous to have a means to relieve some of the pressure build-up within the sheath lumen.

Accordingly, there remains a need for an easy-to-use, sanitary and disposable catheterization assembly. Such an assembly would be well received it if includes a flexible sheath capable of protecting the catheter from contamination, is capable of containing a lubricant or a wetting agent in the case of a hydrophilic catheter, is capable of being gathered to advance the catheter, and is capable of deterring excessive pressure build-up within the sheath lumen when the sheath is gathered.

SUMMARY OF THE INVENTION

These and other needs in the art are addressed in one embodiment by a urinary catheter assembly. In an embodiment, the catheter assembly comprises a catheter including a first end having a urine inlet, a second end having a urine outlet, and a urethra insertable portion. In addition, the catheter assembly comprises a pliable sheath including a lumen, wherein the sheath encloses all or a portion of the insertable portion. Further, the catheter assembly comprises one or more vents in fluid communication with the lumen and an environment outside the lumen.

The foregoing has broadly outlined certain features of the embodiments described herein in order that the detailed description that follows may be better understood. Additional features will be described hereinafter. It should be appreciated by those skilled in the art that the conception and the specific embodiments disclosed may be readily utilized as a basis for modifying or designing other devices, methods, or systems for carrying out the same purposes of the embodiments disclosed herein. It should also be realized by those skilled in the art that such equivalent constructions do not depart from the spirit and scope of the invention as set forth in the appended claims.

BRIEF DESCRIPTION OF THE DRAWINGS

FIG. 3A is a partial side view of a vented sheathed catheter assembly according to another embodiment of the invention.

FIG. 3B is an enlarged cross-section taken along lines 6-6 of FIG. 3A.

FIG. 4A is a partial side view of a vented sheathed catheter assembly according to another embodiment of the invention.

FIG. 4B is an enlarged cross-section taken along lines 7-7 of FIG. 4A.

DETAILED DESCRIPTION OF THE INVENTION

Figure 1A:
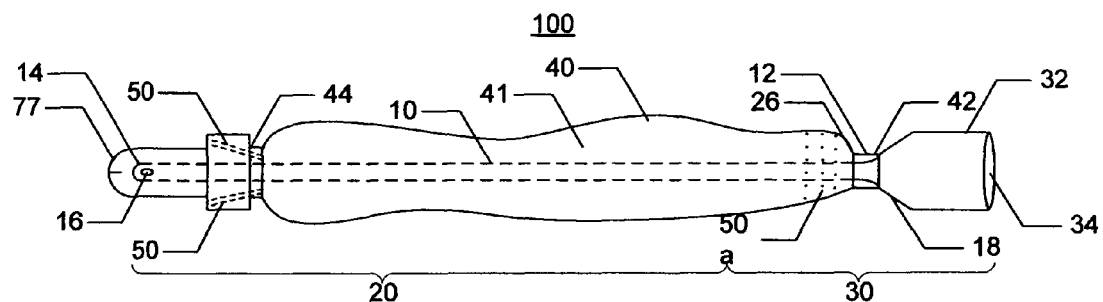
FIG. 1A is a side view of an embodiment of a vented sheathed catheter assembly.

The following discussion is directed to various embodiments of the invention. The embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular system components. As one skilled in the art will appreciate, different persons may refer to a component by different names. This document does not intend to distinguish between components that differ in name but not function. The drawing figures are not necessarily to scale. Certain features of the invention may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections.

U.S. Pat. No. 6,090,075 (House I), U.S. App. No. 60/708,893 (House II), and U.S. application Ser. No. 11/326,699 (House III), are each hereby incorporated herein by reference in their entirety.

Referring to FIG. 1A, an embodiment of a vented sheathed catheter assembly 100 is shown. Assembly 100 comprises a flexible catheter 10 and a protective sheath 40. Catheter 10 includes an insertable portion 20 (intended to be inserted into a patient's urethra) and a non-insertable portion 30 (not intended to be inserted into the patient). Urethra-insertable portion 20 commences at a catheter tip 14, which contains one or more urine inlet(s) 16, and ends at an insertion stop location 26, adjacent non-insertable portion 30.

Catheter 10 further comprises a tip 14, a distal end 32 including a urine outlet 34, and a through bore (not shown in FIGS. 1A-C) that permits fluid communication between inlet (s) 16 and a urine outlet 34. When sufficiently inserted into a patient's bladder, catheter 10 allows urine to drain from the patient's bladder through inlet(s) 16, through the central bore of catheter 10, and exit catheter 10 at outlet 34. Optionally, a urine collection bag may be pre-attached or may be attached by the user such that outlet 34 may be in fluid communication with the collection bag (e.g., FIGS. 5A and 5B).

It is to be understood that "distal" and "proximal" as used herein refer to locations relative to the patient when the catheter assembly is in use. In particular, "distal" refers to locations relatively away from the patient, while "proximal" refers to positions relatively near the patient. For example, the distal end of sheathed catheter assembly 100 is the end of catheter assembly 100 relatively away from the patient (e.g., distal end 32), and the proximal end of sheathed catheter assembly 100 is the end of catheter assembly 100 relatively near the patient (e.g., tip 14).

Figure 1B:
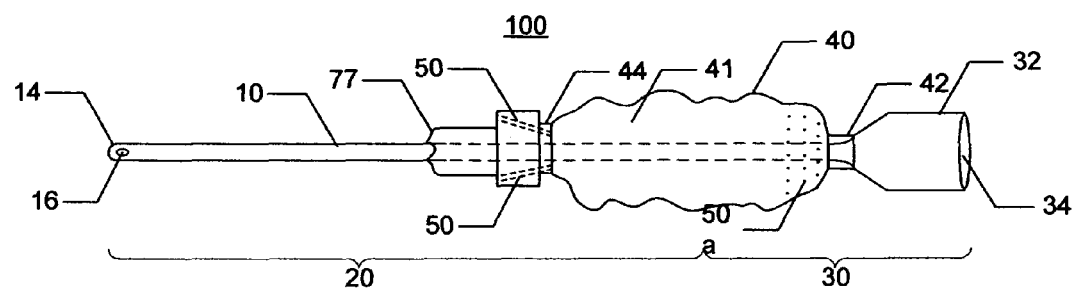
FIG. 1B is a side view of the vented sheathed catheter assembly of FIG. 1A, with the sheath partially gathered.
Figure 1C:
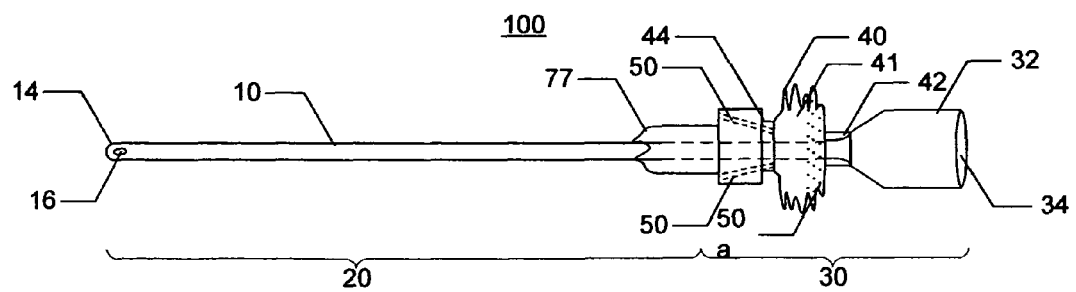
FIG. 1C is a side view of the vented sheathed catheter assembly of FIG. 1A, with the sheath substantially gathered.

In the embodiment illustrated in FIGS. 1A-C, catheter tip 14 initially rests inside, and is supported by, an introducer 77. Introducer 77 slidingly engages insertable portion 20 of catheter 10. Further, introducer 77 includes one or more vents 50 in fluid communication with lumen 41 and the environment outside sheath 40. In the embodiment shown in FIGS. 1A-C, vents 50 are passageways through introducer 77.

Catheter 10 may be any flexible catheter. Further, catheter 10 may comprise any suitable material including without limitation, vinyl, red rubber latex, silicone elastomer, and the like. The urethra-insertable portion 20 of catheter 10 is generally the length of catheter that may be appropriately inserted into the patient's urethra in order to perform a successful urinary catheterization. In select embodiments, the length of insertable portion 20 is about $2/3^{rds}$ the length of catheter 10, and the length of non-insertable portion 30 is about $\frac{1}{3}^{rd}$ the length of catheter 10. The actual length of catheter 10, and the length of the insertable portion 20, may depend on a variety of factors including without limitation, the application of catheter 10 (e.g., adult or child size), the patient's physiology, or combinations thereof. As a practical matter, the length of catheter 10 available for insertion (e.g., insertable portion 20) is decreased, at least to some extent, by the distance on catheter 10 required to accommodate introducer 77 (if provided) and sheath 40 when sheath 40 is gathered near second sheath terminus 42.

Sheath 40 comprises a first sheath terminus 44 coupled to introducer 77 and a second sheath terminus 42 coupled to catheter 10 at attachment point 12. Attachment point 12 is positioned between tip 14 and a distal end 32. In other embodiments, first sheath terminus 44 may not be coupled to an introducer or other tip cover, but rather partially or completely enclose tip 14. In certain embodiments, attachment point 12 is located about $\frac{2}{3}^{rds}$ the length of catheter 10 from tip 14.

In the embodiments shown in FIGS. 1A-C, second sheath terminus 42 is fixed to catheter 10 at attachment point 12 so as to prevent rotational and translational movement of second sheath terminus 42 relative to catheter 10. Second sheath terminus 42 may be fixed to catheter 10 at attachment point 12 by any suitable means including without limitation, by a collar, by an adhesive, by heat pressing, or combinations thereof. In other embodiments, second sheath terminus 42 may not be fixed to catheter 10 (e.g., FIG. 4A). For instance, second sheath terminus 42 may slidingly engage catheter 10. In addition, second sheath terminus 42 and attachment point 12 are positioned at the junction of the insertable portion 20 and non-insertable portion 30 of catheter 10, adjacent distal end 32.

During use of assembly 100, flexible sheath 40 may be gathered as tip 14 and insertable portion 20 are advanced through introducer 77 and into the patient's urethra. Thus, one skilled in the art will appreciate that, in some embodiments, less than all of catheter 10 protected by the sheath 40 may be needed for insertion into the patient. Accordingly, an insertion stop location 26 (where the catheter stops near the urethral opening upon establishment of urine flow) may substantially coincide with attachment point 12, or it may be spaced away from attachment point 12 closer to the tip 14.

In the embodiment of FIGS. 1A-C, sheath 40 encloses all, or at least part of, the insertable portion 20, thereby creating a sheath lumen 41 between sheath 40 and catheter 10. Sheath 40 may comprise any suitable material. In select embodiments, sheath 40 is an elongated, flexible plastic bag. Further, sheath 40 and lumen 41 may comprise any suitable geometry including without limitation, rectangular, cylindrical, flattened, inflated, partially inflated, etc. In the embodiment shown in FIGS. 1A-C, sheath 40 includes a plurality of vents 50$a$ in a distal portion of sheath 40. Vents 50$a$ are in fluid communication with lumen 41 of sheath 40 and the environment outside sheath 40.

Together, introducer 77 and sheath 40 cooperate to enclose and protect catheter 10, insertable portion 20 in particular, from contamination prior to and during use. In the embodiment shown in FIG. 1A, insertable portion 20 of catheter 10 is maintained in sterile condition inside introducer 77 and sheath 40. In alternative embodiments having no introducer 77 or other tip cover, insertable portion 20 of catheter 10 may be enclosed entirely within sheath 40 and thereby maintained in sterile condition.

Still referring to FIG. 1A, during use, introducer 77 is aligned with the patient's urethra. In some embodiments, the proximal tip of introducer 77 may be inserted up to 2 cm into the patient urethra. Tip 14 is then pushed through introducer 77 to advance tip 14 and insertable portion 20 into the patient's urethra. Catheter 10 moves relative to introducer 77 as insertable portion 20 is advanced through introducer 77. As insertable portion 20 is advanced into the patient's urethra, sheath 40 may be gathered as second sheath terminus 42 moves toward first sheath terminus 44, giving catheter assembly 100 an appearance similar to that shown in FIG. 1B. By continuing to advance tip 14 and insertable-portion 20 into the patient's urethra, sheath 40 may continue to gather between second sheath terminus 42 and first sheath terminus 44, giving catheter assembly 100 an appearance similar to that shown in FIG. 1C.

In some sheathed catheter assemblies, the process of gathering sheath 40 to advance insertable portion 20 into the patient's urethra may result in a pressure increase (e.g., a pressure build-up) in lumen 41. This may particularly be a problem in sheathed catheter assemblies in which the sheath lumen is not open ended, not in fluid communication with a urine collection bag, or not in fluid communication with an environment outside the sheath. Without being limited by theory, in sheathed catheter assemblies lacking vents 50 or vents 50$a$, as sheath 40 is gathered, the volume within lumen 41 may decrease. Fluid (e.g., air, wetting agent, etc.) within lumen 41 may become trapped and compressed within lumen 41 as the volume of lumen 41 decreases. The compression of the contents of lumen 41 may result in a pressure increase within lumen 41 relative to the environment outside assembly 100 (e.g., sheath 40 may "balloon-up" as it is gathered between second sheath terminus 42 and first sheath terminus 44).

Slight to moderate pressure build-ups may present minor or no problems at all. However, in some cases, excessive pressure build-up within lumen 41 may lead to undesirable consequences. For instance, a pressure build-up in lumen 41 may result in a force opposing the continued advancement of insertable portion 20 through introducer 77 and into the patient's urethra. This force may act to push introducer 77 towards tip 14. In addition, a pressure build-up within lumen 41 may cause sheath 40 to "balloon-up," which may detrimentally impact the ability of the user to grasp the catheter enclosed by sheath 40. For example, a pressure build-up in lumen 41 may result in some expansion (e.g., increase in the diameter) of lumen 41, which may render catheter 10 somewhat more challenging to handle, position, and/or manipulate. Further, a very high pressure build-up within lumen 41 may result in a tear or rupture of sheath 40. For example, if a user continues to advance insertable portion 20 and gather sheath 40 as sheath 40 "balloons-up," at some point, the material comprising sheath 40 may rupture (e.g., "pop") or a connection between sheath 40 and catheter 10 may fail. Either event may undesirably reduce the ability of sheath 40 to prevent contamination of catheter 10. For example, if sheath 40 is torn, direct contact with insertable portion 20, before insertable portion 20 is placed inside the patient, may be possible.

However, by including vents 50 in introducer 77 and vents 50$a$ in lumen 41, pressure within lumen 41 may be relieved as fluid (e.g., air) compressed in lumen 41 may escape lumen 41 through vents 50 and vents 50$a$. In this manner, vents 50 and vents 50$a$ may deter an excessive pressure build-up within lumen 41 as sheath 40$a$ is gathered between second sheath terminus 42 and first sheath terminus 44 as illustrated in FIGS. 1A-C. In the embodiment of FIGS. 1A-C, vents 50 are passageways through introducer 77 and vents 50$a$ are a plurality of relatively small apertures in sheath 40. In some embodiments, the plurality of vents 50a may form an array or organized pattern. Further, vents 50a are preferably small enough to permit fluid to escape yet still protect insertable portion 20 from contacting non-sterile surfaces.

Figure 2A:
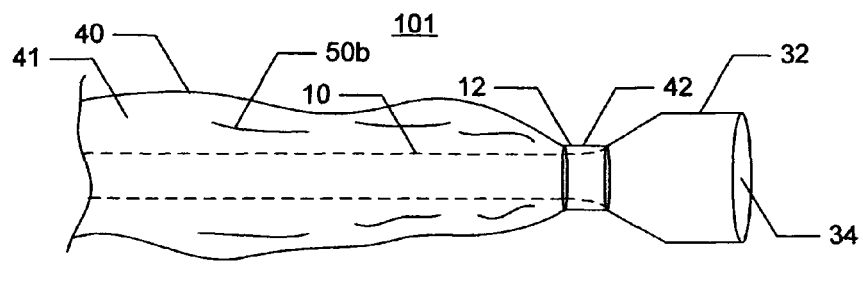
FIG. 2A is a partial side view of a vented sheathed catheter assembly according to one embodiment of the invention.

FIGS. 2A-C, 3A, 3B, 4A, and 4B illustrate alternative variations of vented sheathed catheter assemblies, showing a variety of vents. Referring to FIG. 2A, a partial view of an embodiment of a sheathed catheter assembly 101 is shown. Assembly 101 comprises a flexible catheter 10 and a sheath 40. Catheter 10 includes a distal end 32, an insertable portion 20, and a non-insertable portion 30. Sheath 40 is coupled to a second sheath terminus 42 that is coupled to catheter 10 at attachment point 12. In this embodiment, second sheath terminus 42 is coupled to catheter 10 by a collar that surrounds catheter 10 at attachment point 12. Sheath 40 encloses all, or at least part of, the insertable portion 20 within a lumen 41.

Sheath 40 illustrated in FIG. 2A comprises a plurality of vents 50b. Vents 50b permit fluid communication between lumen 41 and the environment outside sheath 40. In this manner, vents 50b may deter a pressure build-up within lumen 41 as sheath 40 is gathered as illustrated in FIGS. 1A-C. For instance, when catheter 10 is in use and sheath 40 is gathered, some pressure build-up within lumen 41 may be relieved as fluid within lumen 41 is allowed to pass out of lumen 41 through vents 50b. One or more vents 50b may be provided. Vents 50b are preferably sized to adequately relieve pressure within lumen 41, yet minimize and/or prevent physical contact of catheter 10 through sheath 40.

Vents 50b shown in FIG. 2A are slits in sheath 40. However, generally, vents may be any suitable geometry including without limitation, slits, holes (e.g., FIG. 2C), perforations (FIGS. 1A-C), and the like. Further, vents 50b shown in FIG. 2A are positioned along the length of sheath 40. However, generally, vents may be positioned at any suitable location including without limitation, along the entire length of sheath 40 (e.g., FIG. 2A), near the distal end of sheath 40 (e.g., FIGS. 2B and 2C), near the proximal end of sheath 40 (e.g., near first sheath terminus 44), in a collar that couples sheath 40 to catheter 10, in an introducer (e.g., introducer 77), or combinations thereof.

Figure 2B:
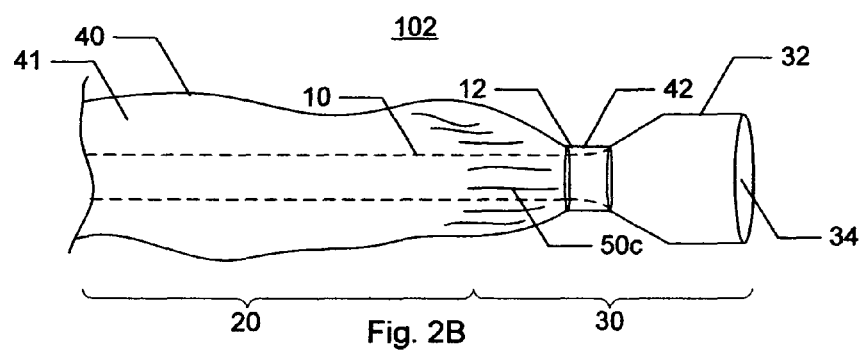
FIG. 2B is a partial side view of a vented sheathed catheter assembly according to another embodiment of the invention.

Referring to FIG. 2B, another embodiment of a sheathed catheter assembly 102 is illustrated. Vents 50c comprise a plurality of slits provided in sheath 40 near second sheath terminus 42. By locating vents 50c near second sheath terminus 42, any possible contamination of catheter 10 through vents 50c may be localized near second sheath terminus 42. Although contamination of catheter 10 is generally undesirable, if any contamination of catheter 10 is to occur, it is preferred that such contamination occur as far as possible from catheter tip end 14, since more distal portions of catheter 10 are least likely to be inserted into a patient's urethra.

Figure 2C:
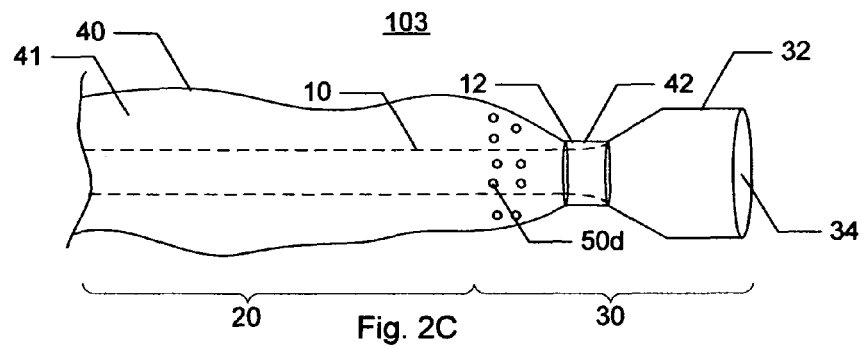
FIG. 2C is a partial side view of a vented sheathed catheter assembly according to another embodiment of the invention.

Referring to FIG. 2C, another embodiment of a sheathed catheter assembly 103 is illustrated. Vents 50d comprise a plurality of holes in sheath 40 near second sheath terminus 42. Similar to the embodiment illustrated in FIG. 2B, in this embodiment, vents 50d are positioned near the portion of catheter 10 least likely to come into contact with a patient when in use (e.g., about non-insertable portion 30).

Figure 2D:
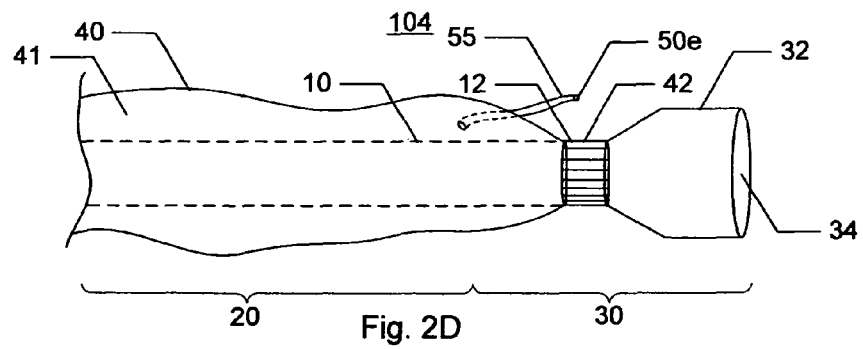
FIG. 2D is a partial side view of a vented sheathed catheter assembly according to another embodiment of the invention.

Referring to FIG. 2D, another embodiment of a sheathed catheter assembly 104 is illustrated. Vent 50e comprises a single hollow tubular 55 provided through and across sheath 40. Vent 50e is essentially the through bore of tubular 55. Thus, vent 50e is in fluid communication with lumen 41 of sheath 40 and the environment outside sheath 40. Tubular 55 may be connected to sheath 40 by any suitable means including without limitation, by heat pressing, adhesive, molded as part of sheath 40, or combinations thereof. In the embodiment shown in FIG. 5D, vent 50e is positioned near the portion of catheter 10 least likely to come into contact with a patient when in use (e.g., near second sheath terminus 42). In other embodiments, one or more tubular 55 including a vent 50e may be provided in any suitable location in sheath 40 including without limitation, at the distal end of sheath 40, along the length of sheath 40, at the proximal end of sheath 40, or combinations thereof. In addition, in the embodiment shown in FIG. 2D, second sheath terminus 42 is fixed to catheter 10 at attachment point 12 by heat pressing sheath 40 to catheter 10.

Referring to FIG. 3A, a partial view of another embodiment of a vented sheathed catheter assembly 105 is shown. Assembly 105 comprises a flexible catheter 10 and a protective sheath 40. Catheter 10 includes a distal end 32, an insertable portion 20, and a non-insertable portion 30. Second sheath terminus 42 is coupled to a collar 43. Collar 43 is coupled to catheter 10 at attachment point 12. Sheath 40 encloses all, or at least part of, the insertable portion 20 within a lumen 41.

In the embodiment illustrated in FIG. 3A, collar 43 is fixed to catheter 10 to prevent translational and rotational motion of collar 43 relative to catheter 10. In different embodiments, collar 43 may not be translationally and rotationally fixed relative to catheter 10.

As best seen in FIG. 3B, collar 43 is physically attached to catheter 10. Catheter 10 includes a through bore 11 in fluid communication with urine inlets at the catheter proximal tip and in fluid communication with outlet 34. Collar 43 comprises four vents 50f. Vents 50f are passages extending through collar 43. In general, vents 50f in collar 43 permit fluid communication between lumen 41 and the environment outside sheath 40. Thus, vents 50f may permit fluid within lumen 41 (e.g., air) to escape lumen 41. In this manner, vents 50f may deter a pressure build-up within lumen 41 as sheath 40 is drawn back towards catheter distal end 32.

In other embodiments, collar 43 may include any suitable number of vents 50f (e.g., one, two, three or more vents 50). Vents 50f are provided across or through collar 43 and spaced evenly about collar 43. In other embodiments, vents 50f may not be spaced evenly about collar 43. Although vents 50f shown in FIG. 3B have a circular cross-section, in general, vents 50f may be any suitable geometry including without limitation, circular cross-section (e.g., FIG. 3AC), rectangular cross-section, or combinations thereof. Further, vents 50f are preferably sized to sufficiently relieve pressure within lumen 41, yet minimize and/or prevent physical contact of catheter 10 through collar 43.

Vents 50f may be provided in any suitable location of collar 43. Still further, vents similar to vents 50f may be provided in a collar that couples first sheath terminus 44 to introducer 77 illustrated in FIGS. 1A-C.

Still referring to FIGS. 3A and 3B, vents 50f are provide in collar 43 near second sheath terminus 42. By locating vents 50f near second sheath terminus 42 and distal end 32, any possible contamination of catheter 10 through vents 50f may be localized near the distal end of catheter 10 (e.g., the portion of catheter 10 least likely to contact the patient).

Referring to FIGS. 4A and 4B, a partial view of another embodiment of a vented sheathed catheter assembly 106 is shown. Second sheath terminus 42 is coupled to a collar 43. Collar 43 is coupled to catheter 10. A single vent 50g results from an annular gap that arises between collar 43 and catheter 10 since the inside diameter of collar 43 is greater than the outside diameter of catheter 10. Thus, in this embodiment, collar 43 is not fixed to catheter 10, but rather slidingly engages catheter 10. Similar to the embodiment illustrated in FIGS. 3A and 3B, in this embodiment, vents 50g are position near the portion of catheter 10 least likely to come into contact with a patient when in use (e.g., near second sheath terminus 42 and distal end 32).

In FIGS. 1A-C and 2A-C, vents 50a, b, c, and d are provide in sheath 40. In FIG. 2D, a vent 50e is provided across sheath 40 in the form of a tubular 55. In FIGS. 3A, 3B, 4A, and 4B, vents 50f and g are provided in collar 43 (e.g. second sheath terminus 42). In different embodiments, vents may be provided in any suitable location allowing pressure within sheath lumen 41 to be relieved. Suitable locations may include without limitation, one or more vents in a collar coupling the sheath to the catheter (e.g., collar 43), one or more vents in the sheath (e.g., vents 50c in sheath 40 shown in FIG. 2B), one or more vents in the introducer or tip cover provided in the proximal tip of the catheter, one or more vents in a collar coupling the sheath to the proximal end of the catheter, or combinations thereof.

Figure 5A:
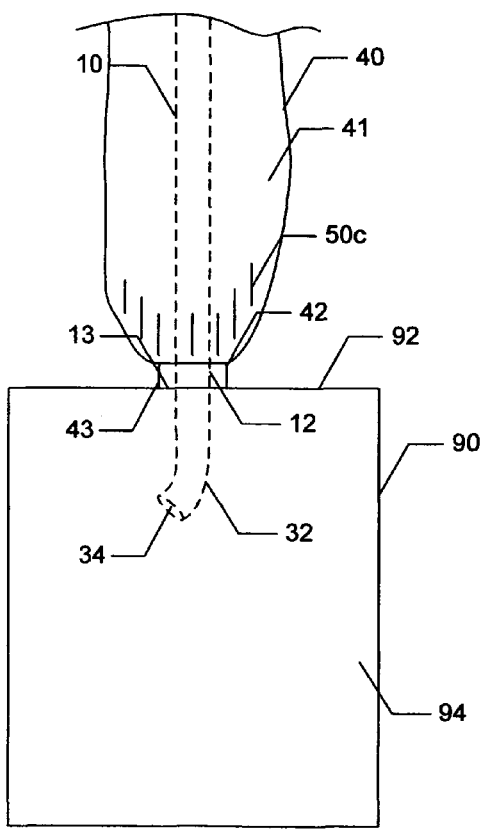
FIG. 5A is a partial side view of a vented sheathed catheter assembly including a urine collection receptacle.

Referring to FIG. 5A, an embodiment of a vented sheathed catheter assembly 107 comprises a urine collection receptacle 90. Urine collection receptacle 90 may be removably attached, permanently attached (non-removable), or integral to assembly 107. Collection receptacle 90 may be constructed of any suitable material. Collection receptacle 90 is preferably made of a flexible, water-proof material (e.g., plastic) and is sized to hold a volume of urine in the range of 700-2000 mL, preferably about 1000 mL.

Collection receptacle 90 comprises a terminus 92 and a lumen 94. Distal end 32 of catheter 10, having a urine outlet 34, is positioned inside a lumen 94 of urine receptacle 90. In this manner, urine may flow from a patient's bladder, through catheter 10 and out of catheter outlet 34 into lumen 94 of urine collection receptacle 90. In this manner, urine may drain from outlet 34 into lumen 94 of collection receptacle 90. In some embodiments, a simple opening (not shown) in terminus 92 may permit distal end 32 to pass into lumen 94. In the embodiment illustrated in FIG. 5A, terminus 92 is coupled to collar 43 at a receptacle attachment point 13. Receptacle attachment point 13 may be any suitable geometry for permitting collection of urine from catheter 10. For example, receptacle attachment point 13 may include without limitation, a collar or band that mates with collar 43 to create a secure water-tight seal/attachment, a hole adapted to connect collection receptacle 90 to collar 43, or combinations thereof.

Assembly 107 further comprises vents 50c in sheath 40. Vents 50c are positioned near second sheath terminus 42. As discussed above, vents 50c provide a means to relieve pressure within sheath lumen 41.

Depending on the location of one or more vents, lumen 41 of sheath 40 may or may not be in fluid communication with lumen 94 of collection receptacle 90. For example, in FIG. 5A, lumen 41 of sheath 40 is not in fluid communication with lumen 94 of receptacle 90. However, in other embodiments, lumen 41 of sheath 40 may be in fluid communication with lumen 94 of receptacle 90. For example, a portion of sheath 40 may be placed within urine receptacle 90 such that one or more vents provided in sheath 41 may be positioned partially or completely within collection receptacle 90. In another example, one or more vents may be provided in sheath terminus 42 or in a collar 43 that are in fluid communication with lumen 94 of collection receptacle 90.

Figure 5B:
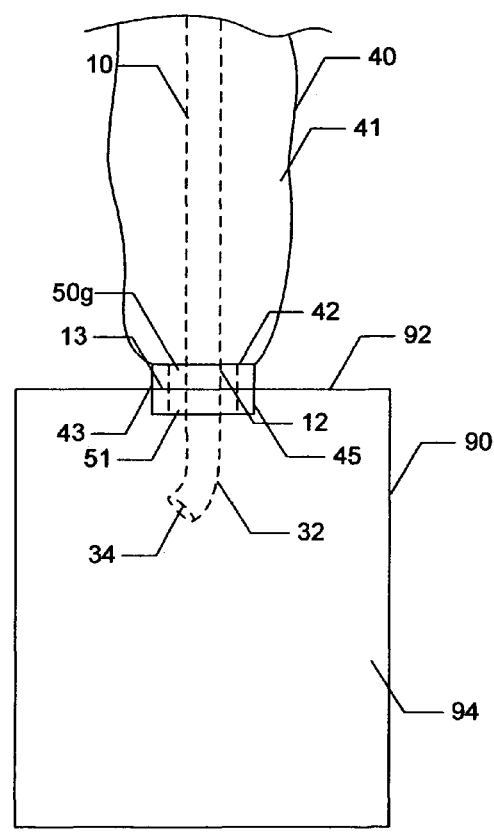
FIG. 5B is a partial side view of another vented sheathed catheter assembly including an attached urine collection receptacle.

Referring to FIG. 5B, another embodiment of a vented sheathed catheter assembly 108 comprising a urine collection receptacle 90 is illustrated. Collection receptacle 90 may be removably attached, permanently attached (non-removable), or integral to assembly 108. Collection receptacle 90 may be constructed of any suitable material. Collection receptacle 90 is preferably made of a flexible, water-proof material (e.g., plastic) and is sized to hold a volume of urine in the range of 700-2000 mL, preferably about 1000 mL.

Collection receptacle 90 comprises a terminus 92 comprising a mating receptacle collar 45. Receptacle collar 45 is coupled to collar 43 at receptacle attachment point 13. In some embodiments, receptacle attachment point 13 may form a water-tight seal between collar 43 and mating receptacle collar 45. In different embodiments, no mating receptacle collar or band is provided in collection receptacle 90 and distal end 32 may simply pass through a hole provided in terminus 92.

Still referring to FIG. 5B, distal end 32 of catheter 10, including a urine outlet 34, is positioned inside lumen 94 of collection receptacle 90. In this manner, urine may flow from a patient's bladder, through catheter 10 and out of outlet 34 into lumen 94.

In the embodiment shown in FIG. 5B, lumen 41 of sheath 40 is in fluid communication with lumen 94 of receptacle 90. Vents 50g provided in collar 43 are in fluid communication with one or more receptacle vents 51 that are provided in mating receptacle collar 45. This arrangement permits fluid communication between lumen 41 of sheath 40 and lumen 94 of collection receptacle 90. In instances when lumen 94 of receptacle 90 has a substantially larger volume than lumen 41 of sheath 40, pressure build-up within lumen 41 may be relieved into lumen 94 of collection receptacle 90 without significantly impacting the operation of receptacle 90 or assembly 108.

Figure 5C:
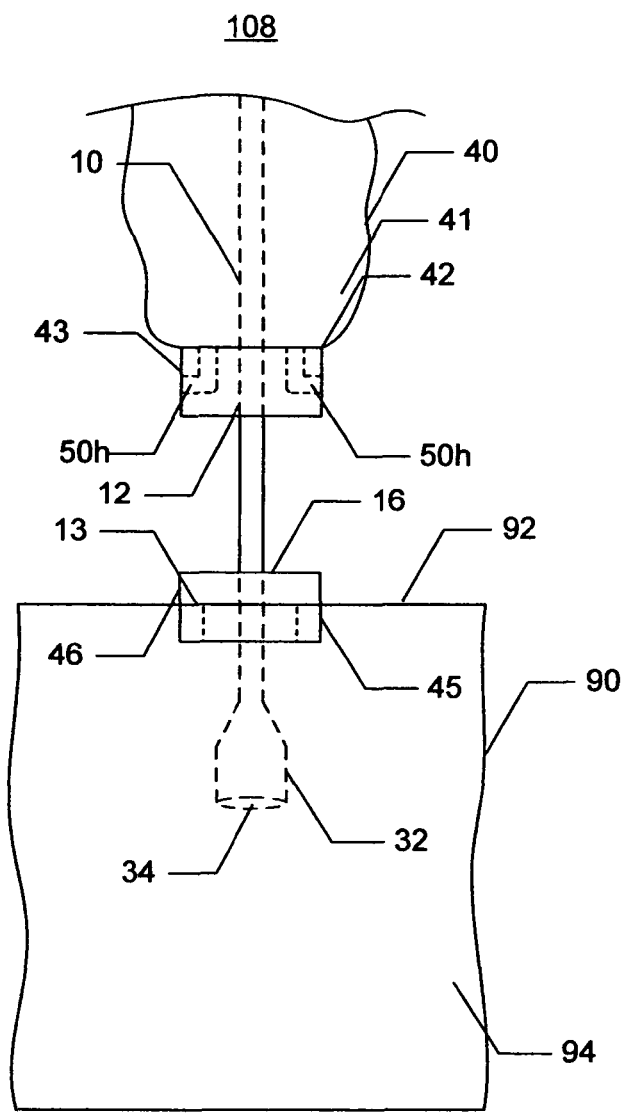
FIG. 5C is a partial side view of another vented sheathed catheter assembly including an attached urine collection receptacle.

Referring to FIG. 5C, another embodiment of a vented sheathed catheter assembly 109 comprising a urine collection receptacle 90 is illustrated. Collection receptacle 90 comprises a terminus 92 comprising a mating receptacle collar 45. Collection receptacle 90 may be removably attached, permanently attached (non-removable), or integral to assembly 109. Collection receptacle 90 may be constructed of any suitable material. Collection receptacle 90 is preferably made of a flexible, water-proof material (e.g., plastic) and is sized to hold a volume of urine in the range of 700-2000 mL, preferably about 1000 mL.

In this embodiment, second sheath terminus 42 is coupled to collar 43, which is fixed to catheter 10 at attachment point 12. In addition, vents 50h are provided in collar 43. Further, a coupling 46 is fixed to catheter 10 at an attachment point 16. Attachment point 16 is distal to collar 43 and distal to attachment point 12. Coupling 46 couples catheter 10 to receptacle collar 45 at a receptacle attachment point 13. In some embodiments, receptacle attachment point 13 may form a water-tight seal between coupling 46 and mating receptacle collar 45. Distal end 32 of catheter 10, including a urine outlet 34, is positioned inside lumen 94 of collection receptacle 90. In this manner, urine may flow from a patient's bladder, through catheter 10 and out of outlet 34 into lumen 94.

Vents 50h are in fluid communication with lumen 41 of sheath 40 and the environment outside sheath 40. However, one of ordinary skill will appreciate that in this embodiment vents 50h may relieve pressure within lumen 41, but do not place lumen 41 in fluid communication with lumen 94 of collection receptacle 90. Thus, fluid within lumen 41 of sheath 40 does not commingle with fluid within lumen 94 of collection receptacle 90.

FIGS. 1A-C show the urethra-contacting end of assembly 100 (proximal end of catheter 10) as including an introducer 77. In the embodiment shown in FIGS. 1A-C, introducer 77 is similar to an O'Neil® type tip with "cross-cut" end. Embodiments of an O'Neil type tip are disclosed in U.S. Pat. No. 4,652,259, which is hereby incorporated herein by reference in its entirety. However, in general, the proximal end of catheter 10 may comprise any suitable configuration. The tip cover or introducer 77 may be similar to those that are known in the art. For example, in some embodiments, introducer 77 may be a introducer similar to that disclosed in House II. Further, in other embodiments, introducer 77 may be replaced with a catheter tip cover to keep at least the insertable portion of the catheter sterile prior to and during use. Still further, in some embodiments, no catheter tip cover is provided and sheath 40 may completely or partially enclose insertable portion 20 of catheter 10. Some alternative configurations for the proximal end of catheter 10 are disclosed in House I, House II, and House III.

Further, in some embodiments, a lubricant or a wetting agent may be included inside the sheath 40, introducer 77, or other catheter tip cover. Such a lubricant or wetting agent may serve to lubricate catheter 10 prior to insertion into the patient's urethra. House I and House II disclose catheter tips and sheaths capable of providing a lubricant or wetting agent to catheter 10.

In addition, distal end 32 of catheter 10 may comprise any suitable geometry. Examples of suitable geometries include without limitation, flared or increased diameter distal end 32 (e.g., FIG. 1A), uniform diameter distal end 32 (e.g., FIG. 5A), decreasing diameter distal end 32, or combinations thereof. Further, in each figure disclosed herein, distal end 32 of catheter 10 extends outside sheath 40. However, in other embodiments, part or all of non-insertable portion 30, including distal end 32, may be enclosed by sheath 40.

In FIGS. 1A-C, 2A-D, 3A, 3B, 4A, 4B, 5A-C of the present disclosure, second sheath terminus 42 is positioned near the junction of the insertable portion 20 and non-insertable portion 30 of catheter 10, adjacent distal end 32. However, in general, second sheath terminus 42 may be positioned at any suitable location. For instance, in some embodiments, second sheath terminus 42 may be coupled to distal end 32 or positioned closer to tip 14. Still further, in some embodiments, second sheath terminus 42 may be fixed to catheter 10 at attachment point 12, while in other embodiments, second sheath terminus 42 may not be fixed to catheter 10.

In light of the present disclosure, one of skill in the art would appreciate that some components of the sheathed catheter assembly could comprise any of a variety of configurations and appearances, as for instance, similar to those disclosed in U.S. Pat. No. 6,090,075 (House I), U.S. App. No. 60/708,893 (House II), and U.S. application Ser. No. 11/326,699 (House III). Further, some of the embodiments disclosed therein include possible variations in the configuration of urine collection receptacle 90.

Catheterization Kit

Figure 6:
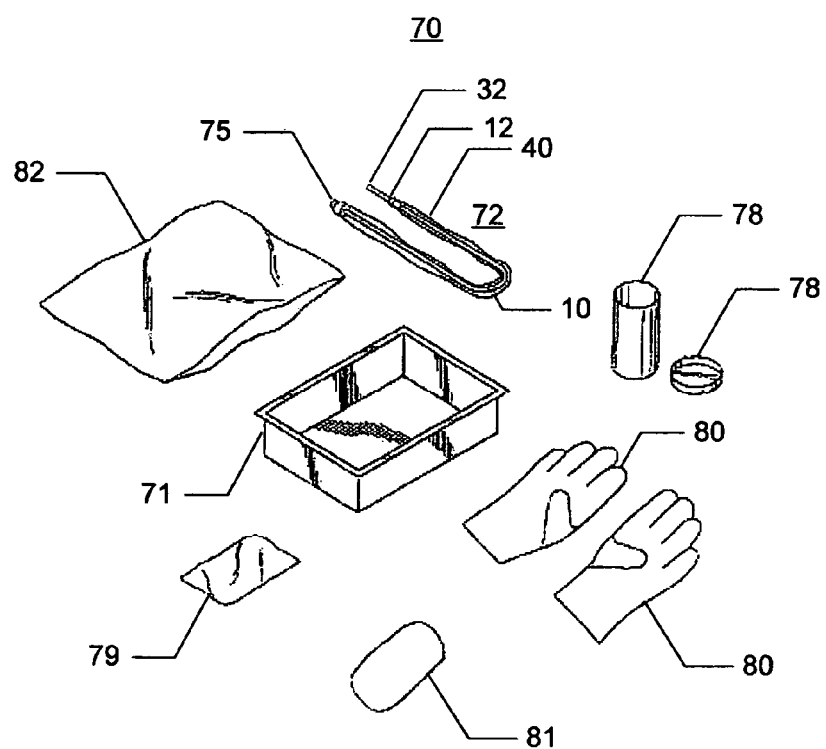
FIG. 6 shows the contents of a catheterization kit according to an embodiment of the present invention.

Referring to FIG. 6, a representative catheterization kit ("cath kit") 70 that is particularly useful for patient catheterizations includes a sheathed catheter assembly 72, representative of those shown and described above as sheathed catheter assemblies 100-109. For example, vented sheathed catheter assembly 72 may include an introducer 77, catheter 10, and sheath 40. Sheath 40 may be attached to introducer 77, if present, and coupled to catheter 10 near the distal end of catheter 10. Further, assembly 72 may include one or more vent(s) (not shown) capable of relieving pressure within the lumen of sheath 40.

In addition to sheathed catheter assembly 72, the kit preferably also contains a packet of antiseptic swabs 79 (e.g., swabs, cotton balls, or the like saturated with Betadine, Povidone-Iodine or other suitable antiseptic), disposable gloves 80, small urine specimen bottle (with cap) 78, and a tray 71 that holds these supplies and also serves as a urine collection container and has a capacity in the range of 700-2000 mL, preferably about 1000 mL. Preferably, a fenestrated drape is also included in the kit. A gauze pad may also be included in the kit as a convenient wipe at the end of the procedure. The kit components are protected by a sanitary wrapper or cover 82. All kit components are preferably disposable.

Absent from the present kit, however, are the customary liquid antiseptic packet, cotton balls, tray for cotton balls, forceps, and packet containing lubricating jelly. In some embodiments, the fenestrated drape is also omitted from the kit without compromising sterile technique. The conventional waterproof absorbent pad is also unnecessary, as it was often included in the past primarily to provide a sterile field for placement of the sterile jelly. Preferably, with use of kit 70, the lubricant is provided within sheathed catheter assembly 72. For example, a sufficient amount of sterile lubricant may be present inside the sheath lumen, or inside an introducer. Alternatively, the catheter may be a lubricated hydrophilic type as is known in the art, in which case the lumen and/or an introducer of the catheter assembly may contain an aqueous wetting agent. A drawback of conventional apparatus and methods is that touching the catheter to any surface outside of the sterile field, as when lubricating jelly is applied, for instance, increases the risk of contamination and urinary tract infection. In contrast, with the present kit, if the sheathed catheter touches anything outside the sterile field, the insertable portion of the catheter remains sterile. Another potential problem associated with conventional catheterization kits and procedures is that, if a glove touches anything outside the sterile field and then touches the catheter, the catheter becomes contaminated. If a sheathed catheter assembly is employed instead, then even if a glove becomes contaminated, the catheter nevertheless remains sterile inside the protective sheath. Thus, the risk of infection and patient morbidity may be reduced or eliminated with use of the new sheathed catheter assembly 72, catheterization kit 70, and catheterization procedure.

The above-mentioned items omitted from conventional catheterization trays are not needed for carrying out a streamlined catheterization procedure with the above-described sheathed catheter assembly 72 and maintaining sterile technique.

Catheterization Procedure

Embodiments of vented sheathed catheter assemblies 100-109 may be used alone or as part of catheterization kit 70. Referring to FIGS. 1A-C, and using assembly 100 in this exemplary explanation, vented sheathed catheter assembly 100 is preferably employed as follows: the user grasps introducer 77 and/or catheter 10 through the soft, flexible sheath 40 near the tip 14 of the catheter to align introducer 77 and tip 14 with the patient's urethra. In the case introducer 77 is an O'Neil® type tip, the projection of introducer 77 may be inserted about 1 to 2 cm into the urethra (or until the perpendicular flange prevents further insertion). Further, in the case where no introducer 77 is provided, if necessary, first sheath terminus 44 may be opened to allow the catheter tip 14 to emerge.

Tip 14 is advanced through introducer 77, if provided, and into the patient's urethra. As tip 14 and insertable portion 20 are advanced, a portion of sheath 40 gathers between first sheath terminus 44 and second sheath terminus 42, giving the catheter assembly an appearance similar to that shown in FIG. 1B. By appropriately repositioning the user's grasp on catheter 10 through sheath 40, and continuing to gently urge insertable portion 20 into the urethra and toward the bladder, the sheath 40 is caused to continue gathering, giving the catheter assembly an appearance similar to that shown in FIG.

1C. Any build-up of pressure within lumen 41 of sheath 40 due to gathering of sheath 40 is relieved through vents 50 and/or vents 50a, thereby deterring some of the undesirable aspects of pressure build-up.

Referring to FIG. 6, when a vented sheathed catheterization assembly (e.g., vented sheathed catheterization assembly 100) is included as part of the catheterization kit 70, catheterization kit 70 is preferably employed as follows: After opening the sanitary wrapper 82, the nurse dons the gloves 80 and places the fenestrated drape, if provided, around the patient's genitalia. The packet 79 containing the antiseptic swabs is opened and the urethral area around the urethral opening is cleansed using the antiseptic swabs. Following proper sanitation, the insertable portion 20 of the vented sheathed catheter assembly is advanced into the patient similar to as described above in reference to FIGS. 1A-C.

When the catheter tip enters the patient's bladder a sufficient distance to commence draining of accumulated urine (e.g., about 1 cm), further insertion ceases.

Prior to commencement of urine drainage, the distal end 32 is placed in fluid communication with tray 71 so that urine can drain into tray 71 while preventing catheter 10 from contacting the collected urine. Alternatively, any other suitable urine receptacle may be used instead of the disposable tray 71 provided as part of kit 70.

After commencement of urine flow, outlet 34 of catheter 10 may be directed briefly into the specimen container 78, to collect a sterile specimen, as needed. Upon completion of urine evacuation, catheter 10 is withdrawn from the urethra and disposed of along with the other components of the kit. If desired, the catheter may be retracted into the sheath prior to disposal. The entire catheterization process can usually be accomplished by a nurse while maintaining sterile technique throughout the procedure.

The disclosed catheterization kit 70 and simplified procedure offers a way to simplify and streamline patient catheterization procedures without compromising sterile technique. Every item that the new kit 70 eliminates from the customary catheterization setup will decrease the number of procedural steps, and also reduces the amount of nursing time needed. Fewer steps also reduces the patient's risk for urinary tract infection, and decreases inconvenience for the patient. Kit 70 is intended to substantially reduce nursing time required to carry out a catheterization procedure.

In the manner described, embodiments of the present invention are intended to offer the potential to improve the convenience and sterility desirable for catheterization procedures. Some embodiments are designed to deter pressure build-up within the lumen of a protective sheath surrounding the catheter. By deterring pressure build-up within the sheath lumen, forces within the lumen which may otherwise operate against retraction of the sheath are reduced. In addition, by reducing pressure build-up within the sheath lumen, the potential for ruptures or tears in the sheath lumen may be reduced, thereby enhancing the ability of the sheath to maintain a sterile catheter. Further, by reducing pressure build-up within the sheath lumen, changes in the bulkiness/geometry of the catheter assembly, which may otherwise render the assembly more difficult to handle, position, and manipulate, may be lessened.

The disclosures of all patents, patent applications, and publications cited herein are hereby incorporated herein by reference in their entirety, to the extent that they provide exemplary, procedural, or other details supplementary to those set forth herein. Further, the discussion of a reference in this disclosure is not an admission that it is prior art to the present invention, especially any reference that may have a publication date after the priority date of this application.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A urinary catheter assembly comprising:
   a catheter comprising a first end having a urine inlet, a second end having a urine outlet, and a urethra-insertable portion;
   a pliable sheath comprising a lumen, wherein the sheath encloses all or a portion of the insertable portion;
   one or more vents in fluid communication with the lumen and an environment outside the lumen; and
   an insertion stop location, wherein the pliable sheath further comprises a terminus coupled to the catheter at a location between the insertion stop location and the second end, the one or more vents present at one or more locations including through a collar formed in the terminus and through the pliable sheath, such that air escapes from the one or more vents as the catheter is inserted and the pliable sheath is gathered, wherein the one or more vents through the collar are passages extending through the structure of the collar, equally spaced about the collar.

2. The catheter assembly of claim 1, further comprising an introducer attached to the sheath opposite the terminus, the introducer and the sheath together enclosing all of the urethra-insertable portion.

3. The catheter assembly of claim 1, further comprising a non-insertable portion, wherein at least part of the non-insertable portion comprises an uncovered region of the catheter outside the sheath.

4. The catheter assembly of claim 1, wherein the terminus sealingly engages the catheter at an attachment point disposed between the insertion stop location and the second end.

5. The catheter assembly of claim 4, wherein the distance along the catheter from the attachment point to the second end is no more than about one-third of the total length of the catheter from the first end to the second end.

6. The catheter assembly of claim 1 wherein the sheath terminus slidingly engages the catheter.

7. The catheter assembly of claim 1, wherein the one or more vents comprise holes.

8. The catheter assembly of claim 1, wherein the one or more vents comprise slits.

9. The catheter assembly of claim 1, wherein the one or more vents comprise an array of apertures.

10. The catheter assembly of claim 1, further comprising a mid-point located substantially halfway between the first end and the second end, wherein the one or more vents are located between the mid-point and the second end.

11. The catheter assembly of claim 1, wherein the portion of the sheath between the first end and the mid-point is substantially free of vents.

12. The catheter assembly of claim 1, wherein each of the one or more vents are located adjacent the terminus.

13. The catheter assembly of claim 1 further comprising a urine receptacle coupled to the non-insertable portion of the catheter.

14. The catheter assembly of claim 1 further comprising a urine receptacle removably coupled to the non-insertable portion of the catheter, wherein the urine receptacle includes a receptacle lumen in fluid communication with the at least one vent.

15. The catheter assembly of claim 1, wherein the one or more vents are adapted to allow a gaseous phase to pass between the lumen and the environment outside the lumen, and adapted to prevent passage of a liquid phase between the lumen and the environment outside the lumen.

* * * * *